United States Patent [19]
Han

[11] 3,946,733
[45] Mar. 30, 1976

[54] MOXIBUSTION APPARATUS

[76] Inventor: Jin Suk Han, 4810 Westminster Ave., Santa Ana, Calif. 92703

[22] Filed: Jan. 13, 1975

[21] Appl. No.: 540,333

[52] U.S. Cl. .............. 128/254; 126/204; 126/15 A; 128/303.1
[51] Int. Cl.² ........................................ A61B 17/36
[58] Field of Search ................. 126/204, 206, 15 A; 128/254, 256, 303.1; 110/72 R

[56] References Cited
UNITED STATES PATENTS

| | | | |
|---|---|---|---|
| 493,967 | 3/1893 | Boyler et al. ............... | 126/15 A UX |
| 1,262,669 | 4/1918 | Hirota ............................ | 128/254 X |
| 1,831,669 | 11/1931 | Kōno ................................. | 128/254 |
| 2,014,868 | 9/1935 | Steele et al. ................... | 126/15 A X |

*Primary Examiner*—Channing L. Pace

[57] ABSTRACT

Therapeutic device for locally topical treatment of the body comprising a skin-applicable open-mouthed combustion chamber, a grating support for herbs or other combustible material and means such as a pressurized air supply and/or a restricted combustion gas outlet to pressurize gases held at the skin by the combustion chamber mouth.

7 Claims, 3 Drawing Figures

U.S. Patent    March 30, 1976    3,946,733
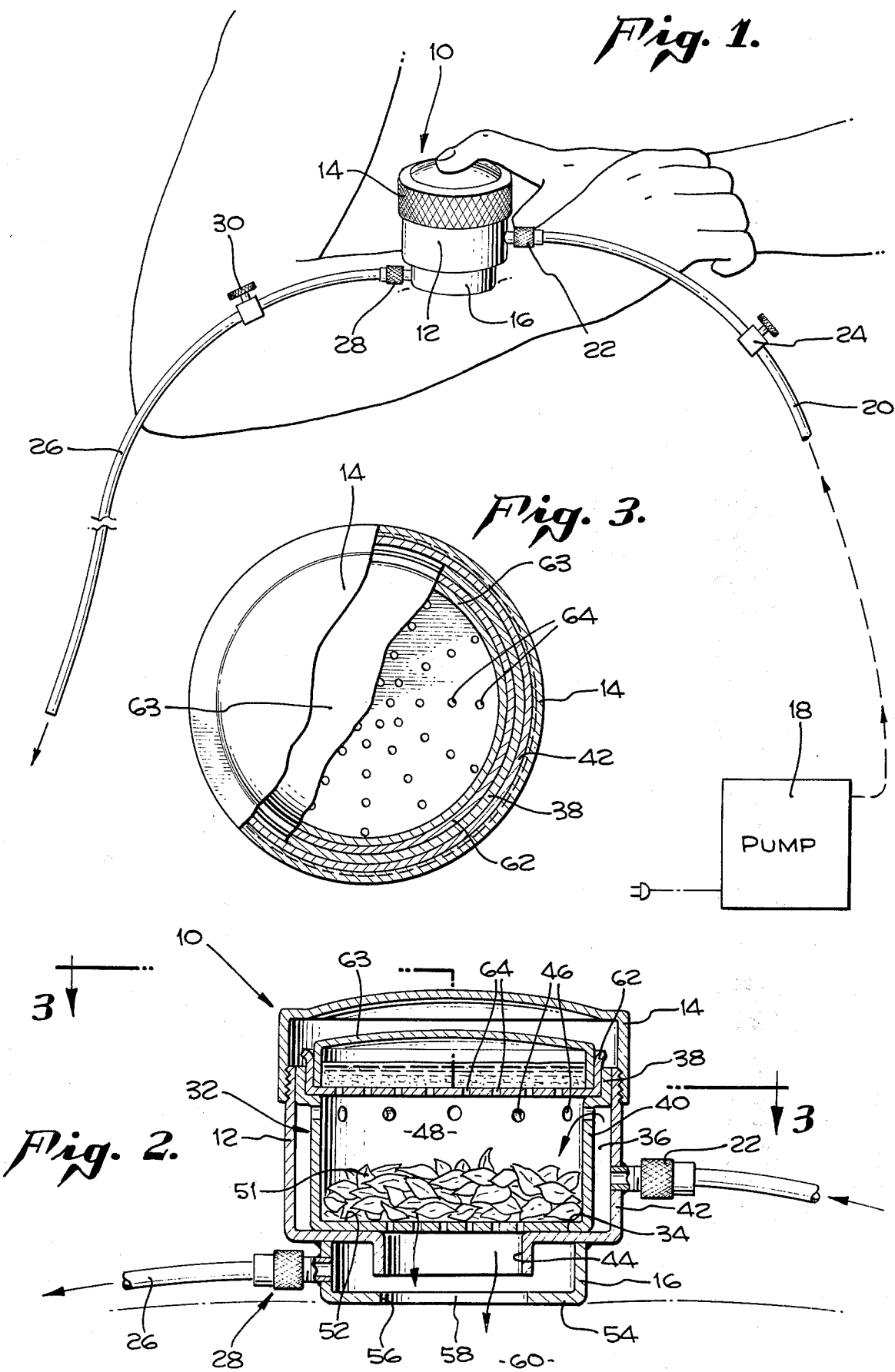

MOXIBUSTION APPARATUS

BACKGROUND OF THE INVENTION

This invention has to do with therapeutic devices and is more particularly concerned with improvements in moxibustion apparatus and like devices for the localized application of therapeutic herbal smoke and gases of combustion to the body of a user, for treatment of bodily ills.

The therapeutic effectiveness of herbs has long been recognized and even today herbal remedies sometimes rival the complex synthetic formulations of modern chemistry is their illness-reducing potency. More recently the localized application of treatment, long practiced as the oriental art of acupuncture for treatment of ills within the body has become popularized and given new recognition for effectiveness.

Moxibustion is a healing art generally involving the localized presentment to the skin of healing combustion products of moxa i.e. generally of the herb Mugwort (*Artemisia vulgaris*). Moxa, more broadly comprises a soft wooly mass prepared from the young leaves of various wormwoods of the Orient or the like, ignited at the skin as a counterirritant or curative treatment.

PRIOR ART

For purposes of topical application of moxibustion products there has been employed a chambered apparatus having a grating spaced from the skin upon which the herbal leaves are burned, the combustion products passing across the skin and freely out of the apparatus through a series of openings formed by a series of arches at the locus of engagement of the apparatus. The area under the arches generally greatly exceeds the grating area. A drawback to this form of treatment application is the inordinate length of time required for a treatment and the need for repeated, lengthy treatment sessions.

SUMMARY

It is an object therefore of the present invention to provide improvements in moxibustion apparatus and particularly to reduce the number of treatments and the period duration of treatments. It is another object to provide a more efficacious use of generated combustion gases, to generate these gases faster, to apply them more efficiently and withal to limit user discomfort. Other objects will appear hereinafter.

Thus and according to the invention, there is provided an apparatus for treatment of a user by periodic localized topical application of therapeutic combustion gases, comprising an open-mouthed combustion chamber adapted to define with the user's skin a topical treatment zone, and means generating therapeutic combustion gases within the chamber, the improvement comprising means pressurizing the gases within the topical treatment zone during treatment periods.

The invention further contemplates provision of means to add therapeutic volatiles to the combustion gases, and use of pressurized air supply to the combustion chamber and/or a restricted gas outlet from the topical treatment zone as the gas pressurizing means.

In a more specific embodiment, apparatus for treatment of a user by periodic localized topical applications of therapeutic combustion gases is provided, comprising a first chamber communicating with a blower pressurized air supply, a second chamber within the first chamber and defining therewith an annular pressurized air supply plenum, the second chamber comprising a combustion chamber having a grating adapted to support for combustion therapeutic gas providing combustible material comprising herbs or the like, a third chamber beyond said combustion chamber grating and adpated to contain combustion gases generated within the combustion chamber, the third chamber having an opening for application of the combustion gases to the user's skin; port means communicating the plenum with the interior of the combustion chamber for passage of pressurized air into the combustion chamber for combustion of the combustible material; the pressurized air acting to differentially pressurize the combustion chamber to urge gaseous combustion products through the grating to the third chamber opening; and reduced gas outlet means in the third chamber to back pressurize the third chamber during treatment periods.

The apparatus may further comprise a blower and means to vary the blower output to correspondingly increase or decrease the pressurized air supply, and the airflow through the combustion chamber parts thereby, to control rate of combustible material combustion. Additionally there may be provided means to variably restrict the gas outlet means of the third chamber to correspondingly vary the back pressurizations of the third chamber.

In highly preferred embodiments, the first chamber is generally cylindrical and provided with an interfitting top, and therebelow an annular shoulder defining a reduced diameter bottom opening. The second chamber is typically likewise cylindrical and of lesser diameter than the first chamber, and is supported within the first chamber on the annular shoulder, the second chamber grating being alined with the first chamber bottom opening. Further there may be provided a bottom opening enclosure structure adapted to rest upon the user's skin, the structure being apertured for skin exposure to gases passing the second chamber grating to and through the first chamber opening and defining the gas outlet means beyond said aperturing. Further, the apparatus may include wall structure between the first and second chambers upwardly defining the annular plenum and a series of circularly distributed parts in the second chamber wall communicating the second chamber interior with the plenum. As in other embodiments, the apparatus may include a supply of therapeutic volatiles supported opposite the grating and open to the second chamber beyond the parts therein, and responsive to chamber combustion heat to deliver the heat generated volatiles into the second chamber, entrained into air-streams passing into the second chamber through the ports to the combustible material.

BRIEF DESCRIPTION OF THE DRAWINGS

The invention will be further described as to an illustrative embodiment thereof in conjunction with the attached drawing in which:

FIG. 1 is a pictorial view of moxibustion apparatus according to the invention in place for treatment on a user's arm;

FIG. 2 is a view in vertical section of the apparatus; and

FIG. 3 is a view in horizontal section, taken on line 3—3 in FIG. 2.

With reference now to the drawing in detail, in FIG. 1 the apparatus is shown at 10 and includes an outer or first chamber 12 having a threaded top closure 14 and a reduced diameter enclosure base structure 16 which may be a continuation of the chamber 12. A pressurized air supply in the form of air pump 18 is provided communicating with the apparatus chamber 12 through tubing 20 and inlet fitting 22. An adjustable base clamp 24 is provided along this tubing 20 for purposes to appear. A second section of tubing 26 is provided, gas outlet communicating enclosure structure 16 through fitting 28 and with the outside atmosphere. A base clamp 30 is provide on tubing 26 for purposes to appear.

With particular reference now to FIGS. 2 and 3, there is provided within the outer or first chamber 12 an inner combustion chamber 32. The combustion chamber 32 defines with the inner surface 12a of the chamber 12 an annular plenum 36, enclosed above by wall 38 being a flared continuation of the vertical wall 40 of chamber 32, and enclosed below by annular shoulder 34 formed as a continuation of the vertical wall 42 of outer chamber 12 to support combustion chamber 32; the shoulder 34 being turned downwardly to form rim 44.

A series of circularly distributed ports 46 is provided at the upper end of chamber 32 above air supply inlet fitting 22, to communicate the interior 48 of the combustion chamber 12 with the plenum 36 and thus serve as a locus of ingress of pressurized air from the pump 18 to the chamber interior. Within the chamber interior 48 is provided at the lower reaches thereof a grating 50 formed centrally of the combustion chamber base 52 on which there is supported a quantity of moxa 51, being herbal leaves as mentioned above. The grating 50 opens downwardly into rim 44. The base enclosure 16 encloses the rim 44 and has further a radially inwardly directed lip 54 which is centrally apertured at 56 to define the topical treatment zone 58 on the user's skin 60. The coaxial, equi-sized relation of zone 58 to rim 44 serves to downwardly direct and concentrate gases emanating through the grating 50 to the skin 60. Gases within the enclosure 16 exit through the outlet fitting 28 and tubing 26 subject to the adjustment of hose clamp 30.

Above the combustion chamber interior 48 there is provided a reservoir chamber 62, supported on flared wall portion 38 of the chamber 32 and containing volatile oils and herbal essences suited to user treatment. These materials are volatilized by the heat of combustion in chamber 12 and the volatile gases enclosed upwardly by cover 63 pass downwardly through holes 64 into the chamber interior 48. The air streams entering the chamber interior 48 through ports 46 entrain and carry downwardly the volatiles from reservoir chamber 62 pass necessarily through grating 50 and are directed by rim 44 to skin surface 60 at zone 58 defined by the opening 56. The contact of the combustion gases in zone 58 effects the therapy. The pressure within the zone 58 builds as additional gases are forced through grating 50 by fresh, incoming air from pump 18. The exit of gas is restricted by virtue of the small outlet fitting 28 and may be further controllably restricted by hose clamp 30 to establish a desired pressurized condition in zone 58; and as required for user comfort.

In operation, the pump 18 is started and a quantity of air, determined by the pump, and throttled by the hose clamp 24, is delivered under superatmospheric pressure into plenum 36. Thence the air passes uniformly, from all radial points through ports 46 into combustion chamber interior 48. Volatiles from reservoir chamber 62 are entrained thereby and carried into the moxa 51 resting upon grating 50. The moxa 51 is lit and the heat of combustion further volatilizes the contents of reservoir chamber 62; the gases of combustion being the therapeutic agent in the apparatus.

The use of the described apparatus provides treatment from 2 to 10 times faster than heretofore known moxibustion apparatus both in duration of treatment periods and in number of such periods. Particularly the apparatus hereof is faster than those having atmospheric pressure merely, at the treatment zone due to unrestricted communication between the treatment zone and the surrounding atmosphere; and the absence of: A pressurized air supply for enhancement of combustion rate; Entrainment of superadded volatiles, and Treatment zone pressurization as well.

I claim:

1. Apparatus for treatment of a user by periodic localized topical application of therapeutic combustion gases, said apparatus comprising a first chamber communicating with a blower pressurized air supply, a second chamber within said first chamber and defining an annular pressurized air supply plenum therewith, said second chamber comprising a combustion chamber having a grating adapted to support for combustion therapeutic gas-producing combustible material comprising herbs or the like, a third chamber beyond said combustion chamber grating and adapted to contain combustion gases generated within the combustion chamber, said third chamber having an opening for application of said gases to the user's skin, port means communicating said plenum with the interior of said combustion chamber for passage of pressurized air into the combustion chamber and for combustion of said combustible material, said pressurized air acting to differentially pressurize the combustion chamber to urge gaseous combustion products through said grating to said third chamber opening, and reduced gas outlet means in said third chamber to back-pressurize said third chamber during treatment periods.

2. Apparatus according to claim 1 including also a blower and means to vary the blower output to correspondingly increase or decrease the pressurized air supply and the airflow through said combustion chamber ports thereby, to control rate of combustible material combustion.

3. Apparatus according to claim 2 including also means to variably restrict the gas outlet means of said third chamber to correspondingly vary the backpressurization of said third chamber.

4. Apparatus according to claim 2 in which: said first chamber is generally cylindrical and provided with an interfitting top and therebelow an annular shoulder defining a reduced diameter bottom opening; said second chamber is generally cylindrical, of lesser diameter than said first chamber and is supported within said first chamber on said annular shoulder, said second chamber grating being alined with said first chamber bottom opening, and including also, bottom opening enclosure structure adapted to rest upon the user's skin, said structure being apertured for skin exposure to gases passing the second chamber grating to and through the first chamber opening and defining said gas outlet beyond said aperturing.

5. Apparatus according to claim 4 including also wall structure between said first and second chamber upwardly defining said annular plenum, and a series of circularly distributed ports in said second chamber wall communicating the second chamber interior with said plenum.

6. Apparatus according to claim 5 including also a supply of therapeutic volatiles open to said second chamber and responsive to chamber combustion heat to deliver said volatiles into said second chamber.

7. Apparatus according to claim 6 in which said volatiles supply is supported opposite said grating and beyond said ports for entrainment of heat-generated volatiles into air-streams passing into the second chamber through said ports to said combustible material.

* * * * *